United States Patent [19]

Kijek et al.

[11] Patent Number: 4,838,894
[45] Date of Patent: Jun. 13, 1989

[54] HAIR DYE COUPLER AND PROCESS FOR MAKING

[75] Inventors: James E. Kijek, Stamford; Keith C. Brown, New Canaan; Bryan P. Murphy, Trumbull, all of Conn.

[73] Assignee: Clairol Incorporated, New York, N.Y.

[21] Appl. No.: 135,572

[22] Filed: Dec. 21, 1987

Related U.S. Application Data

[63] Continuation of Ser. No. 864,734, May 12, 1986, abandoned, which is a continuation-in-part of Ser. No. 762,075, Aug. 2, 1985, abandoned.

[51] Int. Cl.$^4$ .......................... A61K 7/13; C07C 93/06; C07C 91/44
[52] U.S. Cl. ............................................ 8/412; 8/421; 564/353; 564/354; 564/442; 564/443
[58] Field of Search ................ 564/353, 354, 442, 443; 8/412, 421

[56] References Cited

U.S. PATENT DOCUMENTS

| | | | |
|---|---|---|---|
| 3,541,323 | 7/1971 | Kalopissis et al. | 8/412 |
| 3,811,831 | 5/1974 | Bugaut et al. | 8/412 |
| 4,180,679 | 12/1979 | Kapoor | 568/586 |
| 4,346,242 | 8/1982 | Spatz | 568/585 |
| 4,588,410 | 5/1986 | Konrad et al. | 564/443 |

OTHER PUBLICATIONS

Lubs, H. A., Editor, "The Chemistry of Synthetic Dyes & Pigments", Reinhold Pub. Co., N.Y. (1955), pp. 670–673.

Primary Examiner—Glennon H. Hollrah
Attorney, Agent, or Firm—Charles Zeller

[57] ABSTRACT

A substituted m-aminophenol coupler useful in hair dyeing having the formula

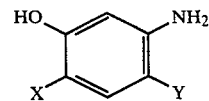

and acid addition salts thereof wherein x and y are selected from the group consisting of halogen and the groups OR of which R is the same or different alkyl, aminoalkyl or hydroxyalkyl groups, at least one of x or y being a group OR and a process for preparing these compounds.

7 Claims, No Drawings

HAIR DYE COUPLER AND PROCESS FOR MAKING

This is a continuing application of application Ser. No. 864,734, filed May 12, 1986, now abandoned, which is a continuation-in-part of application Ser. No. 762,075, filed Aug. 2, 1985, now abandoned.

This invention relates to certain novel meta coupler components useful for oxidation hair dye compositions. More particularly it concerns certain substituted m-aminophenol meta coupler components that are useful for incorporation in oxidation dye compositions, said coupler components being adapted to react with para components under oxidizing conditions to color human hair.

Some m-aminophenols are known to be useful in the hair dye art as meta couplers which will couple with para components under oxidizing conditions to color hair. Many of these, however, have exhibited a number of disadvantages. Some, for example, have proven to be mutagenic as measured by the Ames procedure while others couple with para components as red couplers which are not particularly advantageous. Furthermore, some m-aminophenol couplers require a relative large quantity of oxidizing agent to bring about a complete coupling reaction.

It has now been found that these disadvantages can be eliminated or minimized if there is employed as meta component in oxidation dye compositions one or more meta compounds of the formula

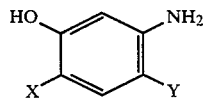

(I)

and acid addition salts thereof wherein x and y are selected from the group consisting of halogen and OR of which R is alkyl, aminoalkyl or hydroxyalkyl; at least one of x or y being OR. R is preferably a lower alkyl, or lower aminoalkyl or lower hydroxyalkyl group having from 1 to 4 or 5 carbon atoms. When x or y is halogen it is preferably chlorine. When both x and y are OR the R in each instance may be the same or different alkyl-aminoalkyl or hydroxyalkyl group.

When R is alkyl, it may be any one of a number of alkyl groups e.g. methyl, ethyl, n-propyl, iso-propyl, n-butyl, iso-butyl, t-butyl, etc. Similarly when R is hydroxyalkyl or aminoalkyl it may also be anyone of a variety of radical e.g. β-hydroxyethyl, β-hydroxypropyl, γ-hydroxylpropyl, α,β-dihydroxylpropyl, β-aminoethyl, etc.

U.S. Pat. No. 4,129,414 discloses polyhalogen 3-aminophenols of the formula

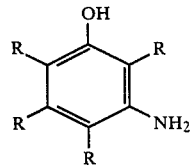

wherein two to three R's are halogen and the remaining one represent hydrogen. These are said to be useful as couplers is hair dye preparation.

U.S. Pat. No. 3,918,896 discloses meta-aminophenol couplers of the formula

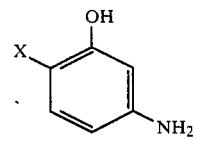

wherein x is a halogen.

U.S. Pat. No. 2,056,299 issued to Sexton is concerned with di-β-alkoxyethyl ethers of aminohydroquinone. These compounds are used in the manufacture of azo dyestuffs, the amino compounds being prepared by the reduction of the corresponding nitro compound.

Two related Kalopissis and Bugaut patents are directed to certain dihydroxyaminophenols and their use in hair dyeing processes. These U.S. Pat. Nos. are 3,546,293 and 3,558,259. It is the essence of the patented compounds that the amino group and a hydroxy group be on adjacent carbon atoms. In many of the disclosed preparative methods the amino compounds are prepared by the reduction of the corresponding nitro compound.

The Dickey U.S. Pat. Nos. 2,537,975; 2,726,251 and 2,391,011 are principally concerned with certain anthraquinone compounds which require the use of certain substituted anilines in their preparation. Thus, the '975 patent dicloses the mono-ethoxylated anilines and discusses their preparation from the corresponding nitro compound. The '251 patent discloses the mono-ethoxylated anilines which may further have hydroxy or methoxy substituents on the ring.

The older Lehmann U.S. Pat. No. 2,095,070 discloses the compound, 5-nitro-1,2,4-trihydroxybenzene.

Quelet, et al. (Compt. Rend. 240 1439 [1955]) reports on the preparation of various ethers of 5-nitro-1,2,4-trihydroxybenzene. The third and fourth supplements of *Beilsteins Handbuch* listing for the nitro compound give some additional ethers of this type.

U.S. Pat. Nos. 3,011,858 (Lantz, et al.) and 3,546,294 (Kalopissis) are concerned with somewhat similar hair dyeing processes. The Lantz '858 patent uses dihydroxyaminobenzenes, such as 2,5-dihydroxyaminobenzene; and 3,4-dihydroxyaminobenzene in its hair dyeing process. In the Kalopissis '294 patent, 2,5-dihydroxy-N-alkyl-aminobenzenes, such as 2,5-dihydroxymonomethylaminobenzene, are used in the hair dyeing process.

Also of interest from the standpoint of hair dyeing processes are three U.S. Patents concerned with the use of trihydroxybenzenes, i.e., 1,2,4-trihydroxybenzene and 2,4,5-trihydroxytoluene. These patents are U.S. Pat Nos. 2,733,186 (de Brye), 2,975,101 (Charle, et al.) and 3,167,478 (Charle, et al.).

Any compound falling within the definition set out above in connection with formula (I) may be used as a meta component in accordance with the present invention. In some instance it may be advantageous to employ a mixture of meta compounds falling within said definition as the meta component. There are however preferred classes of meta compounds which are defined in the formula given below:

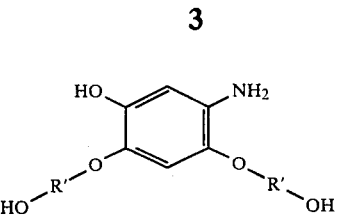

wherein R' is a divalent alkylene radical having 1 to 4 carbon atoms;

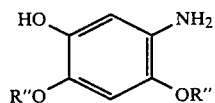

wherein R" is a lower alkyl or lower aminoalkyl radical having 1 to 4 carbon atoms; and

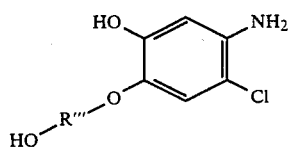

wherein R'" is a divalent alkylene radical having 1 to 4 carbon atoms.

The synthetic route for preparing the meta compounds of this invention is given in Table I below. Several of the intermediate compounds prepared in the course of this synthesis and several of the synthetic steps are novel. The process is illustrated with respect to the preparation of the hydroxyethoxy and the methoxy derivatives. It is to be understood that it is also applicable to the preparation of other compounds falling within the definition given in formula I, II, III and IV above.

phenol-p-toluenesulphonate, is nitrated with fuming $HNO_3$ in step 2 to obtain 2,4-dichloro-5-nitrophenyl-o-nitro-p-toluenesulphonate which is reacted with the piperidine (step 3) to unblock the phenol group (for subsequent benzylation) to produce 2,4-dichloro-5-nitrophenol.

The protection of the phenolic hydroxy group to permit subsequent nucleophilic substitution on the benzene ring presented a special problem. It has been found that this is best accomplished by benzylating the hydroxy group with a benzyl halide e.g. benzyl bromide (step 4). The product of this reaction is O-benzyl-2,4-dichloro-5-nitrophenol. This is used as an intermediate in preparing both the mono and the bis nucleophilic substitution products. In carrying out this reaction, an akali metal salt e.g. the sodium salt of the particular alcohol that is to replace one or two of the chlorine atoms on the benzene ring (e.g., ethylene glycol, methanol, monothanolamine) is reacted with O-benzyl-2,4-dichloro-5-nitrophenol. This reaction takes place in two steps (steps 5 and 6) giving a reaction mixture that contains both the mono and bis substitution products which may be separated from each other by any suitable means.

The final step in the synthesis is a catalytic debenzylation and hydrogenation. This is accomplished by hydrogenating either the mono ether (step 7B) or bis ether (step 7A) compounds in an acidic medium and in the presence of a hydrogenation catalyst e.g. Pd/C.

Another feature of the present invention provides a class of intermediate compounds that are especially useful in preparation of the meta components of this invention. These may be described by the general formula

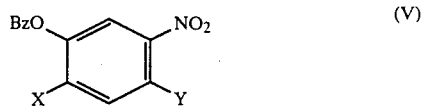

TABLE I

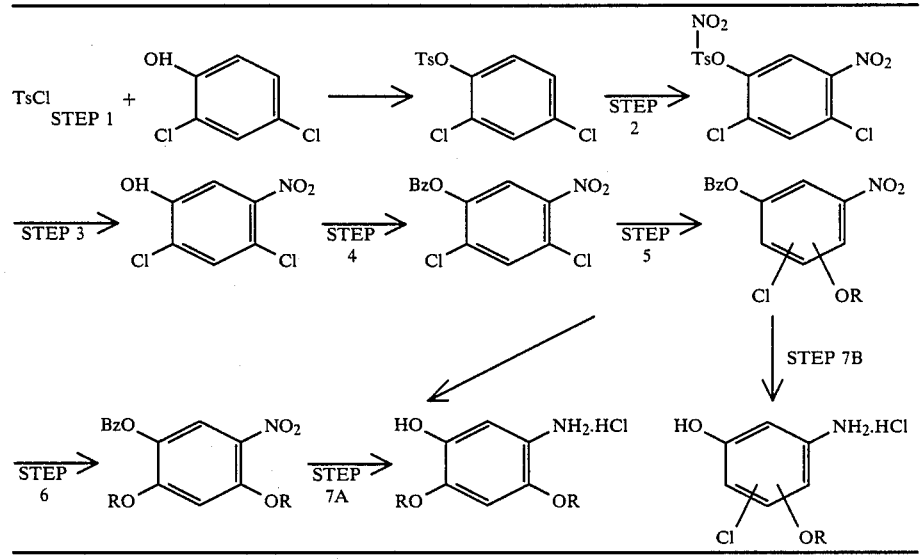

Bz = BENZYL
R = $CH_2CH_2OH$,
R = $CH_3$ or
R = $CH_2CH_2NH_2$

Step 1 is a tosylation reaction and involves reacting p-toluenesulphonyl chloride with the 2,4-dichlorphenol. The product of the reaction i.e. 2,4-dichlorowherein Bz is benzyl, x and y may be the same or different and are selected from the group consisting of halogen and OR; wherein the R is alkyl, or aminoalkyl or hydroxyalkyl. In the preferred cases R is a lower alkyl, aminoalkyl or lower hydroxyalkyl having from 1 to 4 or 5 carbon atoms. When x or y a halogen they are preferably Cl. Of this class of intermediates the preferred compounds are as follows:

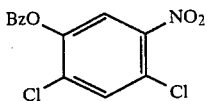
(VI)

wherein Bz is benzyl;

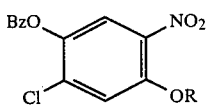
(VII)

wherein Bz is benzyl and R is lower alkyl, lower aminoalkyl or lower hydroxyalkyl having 1 to 4 carbon atoms;

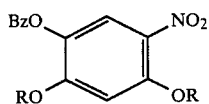
(VIII)

wherein Bz is benzyl and R is the same or a different lower alkyl, aminoalkyl or lower hydroxyalkyl group having 1 to 4 carbon atoms.

The oxidative dye coupler compounds of formula (I) through (IV) according to the invention can be used as such or, preferably, in the form of their salts with inorganic or organic acids. Useful salts include, for example, hydrochlorides, sulfates, phosphates, acetates, propionates, lactates, citrates, and the like.

The hair dye described above in formulas (I) through (IV) are intended for use mainly as meta coupler components in oxidation dye compositions. These are usually aqueous alkaline compositions that contain, in addition to the meta components (coupler) at least one para component (developer). Optionally, such composition may also contain such things as modifier dye intermediates, nitro dyes, soaps, surfactants, thickening agents, antioxidants and organic solvents. Furthermore, these aqueous compositions may take various forms such as solutions, flowable liquids, pastes, creams or gels.

As illustrative of the para components that may be used as the oxidation dye developer in this invention mention may be made of the following:

p-toluenediamine, p-aminophenol, p-aminodiphenylamine, 4,4′-diaminodiphenylamine, 2,6-dimethyl-p-phenylenediamine, 2,5-diaminopyridine.

The class of para components described in the following formula:

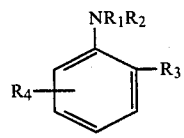
(IX)

or its non-toxic salts, in which:
$R_1$ is hydrogen, alkyl or hydroxyalkyl;
$R_2$ is hydrogen or hydroxyalkyl;
$R_3$ is hydrogen, alkyl, alkoxy or halogen; and
$R_4$ occupies any of the remaining positions on the benzene radical and is hydrogen, alkyl, alkoxy or halogen; are or particular value. Para components of formula IX in which $R_2$ is hydrogen when $R_3$ is alkyl, alkoxy or halogen and providing that at least two of $R_1$, $R_2$, $R_3$ or $R_4$ are other than hydrogen, are of special interest. In this case too, the alkyl groups or alkyl moieties contain 1 to 5 carbon atoms and the hydroxyalkyl contains from 1 to 3 hydroxy groups. The halogen may be Cl, Br, F, I, etc., preferably, Cl or Br. p-Phenylenediamine is especially preferred.

In addition to the meta and para components, the oxidation dye compositions of this invention may contain other modifier dye intermediates. These include such things as the other m-aminophenols, compounds containing active methylene groups, phenols, etc. Meta-aminophenols can give either indophenols or indamines on oxidative coupling with para components. The products are usually violet in color and are used in modifying shades. Examples of aminophenols useful herein are 2,4-diaminophenol, m-aminophenol, aminoresorcinol, 1,5-aminohydroxynaphthalene and 1,8-aminohydroxynaphthalene.

Compounds containing active methylene groups are also capable of reacting with the oxidatively activated para components. The products are imino compounds of various types and are yellow or red in color. Examples of active methylene compounds employable in the present invention includes for example, 3-methylpyrazolone-(5), 1-phenyl-3-methylpyrazolone-(5); 1,3-dimethylpyrazolone-(5), acetoacetic acid anilide, benzoylacetotoluide and nicotinoylacetanilide.

Still other oxidation dye intermediates, i.e. modifiers, may be present in the compositions of this invention which produce colored products under oxidative conditions by more complex mechanisms. These may include one or more of selfcoupling, or coupling with the para components or with other intermediates present. Among these may be mentioned hydroquinone, catechol, 1,5-naphthalenediol, o-phenylenediamine, o-aminophenol.

Phenols react with para components, in the presence of oxidizing agents, to produce indophenols. These are usually blue or violet compounds, although resorcinols give yellow or brown colored compounds under these conditions. The brown colors obtained from the reaction of resorcinols are commonly used to produce the depth of a shade. Examples of phenols useful in oxidation dye compositions of this invention are pyrogallol, resorcinol, pyrocatechol and alphanaphthol.

It is sometimes desirable to add to the oxidation dye mixtures dyes which are already colored, i.e. which do not require an oxidizing agent for color development. These are generally added for blending purposes to obtain natural looking colors in the final dyeing operation. One class of dyes which may be used for this purpose is the nitro dyes and this component is generally referred to herein as the nitro dye components. A large number of nitro dyes are known in the art which are suitable for this purpose. The only limitation that is placed on a nitro dye to be useful in the present invention is that it be one whose color is not destroyed by the oxidizing agent used in the final color development of the oxidizable components. By way of illustration of suitable nitro dyes, mentioned may be made of the following:

4-nitro-o-phenylenediamine, 2-nitro-p-phenylenediamine, 4-nitro-2-aminophenol, 5nitro-2-aminophenol, 2-nitro-4-aminophenol and picramic acid.

The pH of the oxidation dye mixture of this invention will generally be on the alkaline side. It is preferred, however, that this pH be in the range of about 8–11.

Any of a wide variety of alkalizing agents can be used to adjust the pH of the dyeing composition on the basic side. Ammonium hydroxide, because of its freedom from toxicity over a wide concentration range and its economy, is an acceptable alkalizing agent, However, they can be used in place of, or together with, ammonia any other compatible ammonia derivative as an alkalizing agent, such as an alkylamine, such as ethylamine, or triethylamine; or alkanolamine, such as monoethanolamine or diethanolamine. Likewise, any other of the common alkalizing agents may be used, such as sodium or potassium hydroxide, sodium or potassium carbonate, sodium phosphate, sodium hydrogen phosphate, sodium silicate, and the like.

Among the soaps which may be present in the compositions of this invention there may be mentioned the sodium, ammonium or potassium salts of lauric, stearic, palmitic, oleic, linoleic or ricinoleic acid. The soaps may be present to the extent of 10 to 35% of the weight of the oxidation dye mixture, and preferably 15 to 25%.

Among the surface active agents useful in the present invention, mention may be made of the water-soluble surface active agents. These can be anionic, non-ionic or cationic. Illustrative of the various types of water-soluble surface active agents there can be mentioned: higher alkylbenzenesulfonates; alkylnaphthalenesulfonates; sulfonated esters of alcohols and the polybasic acids; taurates; fatty alcohol sulfates; sulfates of branched chain or secondary alcohols; alkyl dimethylbenzyl ammonium chlorides; and the like. Illustrative of specific surfactants there can be mentioned: sodium lauryl sulfate; polyoxyethylene lauryl ester; myristyl sulfate; glyeryl monostearate; sodium salt of palmitic methyl taurine; cetyl pyridinium chloride; lauric diethanolamide; polyoxyethylene stearate; stearly dimethyl benzyl ammonium chloride; dodecyl benzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,9-diethyl-tridecanol-6-sulfate and the like. The quantity of water-soluble surface active agent when present can vary over a wide range, such as that of from about 0.5 to about 30% by weight of the composition, and preferably 1 to 10%.

Various organic solvents may also be present in the oxidation dye mixture for the purpose of solubilizing a dye intermediate or any other component which may be insufficiently soluble in water. Generally, the solvent selected is such as to be miscible with water and innocuous to the skin and includes for example, ethanol, isopropanol, glycerine, ethylene glycol, propylene glycol, ethylene glycol monoethyl ether, diethylene glycol, diethylene glycol monoethyl ether, etc. The amount of solvent used may vary from 0 –50% of the oxidation dye mixture, and preferably 10 –35%.

To exemplify the thickening agents that can also be incorporated in the present dyeing composition, mention may be made of sodium alginate or gum arabic or cellulose derivatives such as methycellulose, hydroxyethylcellulose, or the sodium salt of carboxymethylcellulose, or acrylic polymers, such as polyacrylic acid sodium salt, or inorganic thickeners, such as bentonite.

The quantity of thickening agent when present can vary over a wide range, such as that of from about 0.5% to about 5% and preferably from about 0.5% to about 3% by weight.

To illustrate the antioxidants that may be used in the present oxidation dye mixture, mention may be made of sodium sulfite, thioglycolic acid, sodium hydrosulfite, erythorbic acid and ascorbic acid. The quantity of antioxidant that may be contained in the instant oxidation dye mixture will usually be in the range of from about 0.1% to about 1% by weight based on the total weight of the oxidation dye mixture.

Water is ordinarily the major constituent of the present composition and can vary over a wide range dependent in large measure on the quantity of other additives. Thus, the water content can be as little as 20% and preferably from about 30% to about 80%.

The dyeing compositions of this invention are preferably aqueous compositions. The term "aqueous composition" is used herein in its usual generic sense as embracing any water-containing composition embodied in the invention. This includes true solutions or mixtures of the dye in an aqueous medium, either alone or in conjunction with other materials, which are also dissolved or dispersed in the aqueous medium. The dye may be colloidally dispersed in the medium or may merely be intimately mixed therein.

To further illustrate the various other modifiers, antioxidants, alkalizers, thickeners, chelating agents, perfumes and other adjuvants that may be incorporated in the oxidation dye mixture of this invention, reference is made to Sagarin "Cosmetics, Science and Technology" (1957), pages 505-507, Interscience Publishers, Inc., New York. The aqueous compositions of this invention may take many forms. Thus, they may be thin or thick flowable liquids, pastes, creams, gels etc.

To summarize the various components that may comprise the oxidation dye mixture of this invention, Table II is given. The percentages are given as percent by weight based on the total weight of the oxidation dye mixture.

TABLE II

| Components | % by weight | |
|---|---|---|
| | General | Preferred |
| Meta Coupler component (formula I) | 0.05–5.0 | 0.1–1.5 |
| Para developer component | 0.05–5.0 | 0.5–1.5 |
| Other oxidation dye intermediate | 0.05–2.0 | 0.1–1.0 |
| Nitro dyes | 0.1–0.5 | 0.1–0.25 |
| Soap | 10–35% | 15–25% |
| Surfactant | 0.5–30% | 1–10% |
| Thickening Agent | 0.5–5% | 0.5–3.0% |
| Antioxidants | 0.1–1% | 0.5–1.0% |
| Organic solvents | 0–50% | 10–35% |
| Water | QS to 100% | QS to 100% |
| Alkalizing agent to pH | 8 to 11 | 9 to 10 |

The aforesaid oxidation dye mixture of this invention are intended for use in conjunction with conventional oxidizing agent necessary to effect reaction to colored products. Typical oxidizing agents that are useful for this purpose are aqueous solutions of hydrogen peroxide, e.g. 1.5 to 6%, or high viscosity creams containing in addition, for example, nonylphenol polyethylene glycol or lauryl alcohol polyethylene glycol, in an amount of from 2-10% of the weight of oxidizer, or crystalline peroxide, such as urea peroxide or melamine peroxide.

In use, a quantity of the oxidizing agent described above is mixed with a quantity of oxidation dye composition described previously. Usually, the amount of oxidizing agent is far in excess of that required to oxidize the intermediates, the amounts taken being dependent on the form and concentration of the oxidizer selected. However, it is one of the important features of the present invention that with the meta coupler component of formula (I), only about one-half of the amount of oxidizing agent usually used for oxidation dye compositions is required to produce the same degree of coloration. Accordingly, the risk of damage to the hair, roots, and scalp due to the excessive amounts of oxidizing agent can be substantially reduced. Of course, to the extent that other oxidation dye intermediates are used in conjunction with the meta coupler compounds of this invention an actual 50% reduction of the total quantity of oxidizing agent may not be practical. Nevertheless, reductions in amount of oxidizing agent up to about 50%, especially up to about 30% particularly especially from about 5% to 25% can be realized, depending on the meta and para components present in the oxidation dye composition.

In use the mixture is well shaken and applied to hair. It can be applied as a shampoo to the entire head, applied to one area of the hair, such as the roots and combed through the rest of the hair later. The mixture is allowed to remain on the head for a period of time and is then removed by shampooing. The normal time of application is 20–30 minutes, but application times of from 10 minutes to one hour can be used. Room temperature during application is preferred although higher or lower temperatures, e.g. 15°–40° C. can be used.

In one form of application of the compositions of this invention, the oxidation dye mixture is dispensed from an aerosol container under pressure of a suitable propellant. The foam so obtained is mixed with the developer, generally a solution of hydrogen peroxide, and applied to the hair as above.

In a preferred embodiment, the oxidation dye composition, which may be in the form of solution, flowable liquid, paste, cream or gel, is provided in a first container and the stabilized peroxide oxidizing agent is provided separately in a second container, the first and second containers being sold together as a kit for a single application use wherein the contents of the first and second containers are thoroughly mixed together immediately prior to use. The first and second containers may be individual sealed packages or containers of any suitable material inert to the oxidizing composition and oxidizing agent. Alternatively, the first and second containers may constitute separate but isolated compartments of a single container wherein the first and second compartments are isolated by a seal or diaphragm, for example, which can be removed or punctured to allow the contents to be mixed together in one or the other or both of the compartments. Devices of this nature are well known in the art and have the advantage of providing predetermined dosages of the oxidizing agent and dye composition to achieve the desired color effect.

As used herein and in the appended claims, the terms "compartments" and "containers" are used interchangeably to refer to either of these embodiments, namely, separate unconnected receptacles or packages or separate but isolated receptacles of a single unit package. The following Examples are given to further illustrate this invention. It is to be understood, however, that the invention is not limited thereto. Unless otherwise specified temperatures are given in °C.

EXAMPLES 1 and 2

SYNTHESIS

Tosylation of 2,4-dichlorophenol:

To 90.0 g (0.47 moles) of p-toluenesulphonyl chloride in 250 ml dry pyridine was slowly added 76.6 g (0.47 moles) 2,4-dichlorophenol. The temperature of the mixture rose to 40°. A white precipitate formed within minutes. TLC shows the reaction complete within 3.5 hours. The precipitate was collected by vacuum filtration washed with $H_2O$ and dried. The filtrate of the initial collection was poured onto 400 ml ice and the resulting precipitate collected, washed with $H_2O$ and dried. TLC shows the two collections to be the same product. Yield of crop #1 was 94.6 g, m.p. 114°–117° C.; crop #2 was 41.3 g, m.p. 116°–118° C. Combined yield was 135.9 g (91.1%).

Nitration of 2,4-dichlorophenyl-p-toluenesulphonate:

To 1350 ml of fuming $HNO_3$ (d=1.48) cooled in an ice bath to 15° was very gradually added 135.0 g (0.425 moles) of 2,4-dichlorophenyl-o-toluenesulphonate over 30 min with stirring. After 30 min, the mixture was stirred onto 4 L ice. The pale yellow precipitate was collected by filtration and washed with water. Melting point of the crude product was 93°–96°. The product was recrystallized from 3 L absolute ethanol. Yield of the yellow needles was 154.4 g (89.0%), m.p. 100°–101°.

Preparation of 2,4-dichloro-5-nitrophenol:

One hundred and fifty grams (150.0g) (0.37 moles) of 2,4dichloro-5-nitrophenyl-o-nitro-o-toluenesulphonate was heated with 49.97 g piperidine at 100° for 1.5 hours. The solution was alkalized with 1 M NaOH. The oily product that separated solidified within 30 min. This dark orange solid was recrystallized using absolute ethanol. The lightly colored (yellow-brown) 1-o-nitro-o-toluenesulphonylpiperidine needles that crystallized were collected and set aside. The filtrate was acidified with 3 M HCl (aq.). The off-white crystals were collected by filtration, washed with 3 M HCl and dried. Yield of the 2,4-dichloro-5-nitrophenol was 42.1 g (60.6%), m.p. 98°–100° C.

Benzylation of 2,4-dichloro-5-nitrophenol:

To 42.0 g (0.20 moles) of 2,4-dichloro-5-nitrophenol in 1000 ml acetone with 30.41 g (0.22 moles) $K_2CO_3$ was added 23.8 ml [(34.2 g) (0.20 moles)] benzyl bromide. The mixture was refluxed overnight. TLC shows reaction complete. The mixture was cooled to room temperature and the solubles filtered off. The filtrate was reduced to dryness on the roto-vap. Yield of the orange solid was 57.3 g (96.2%). The product was recrystallized from absolute ethanol, m.p. 82°–83° C.

Nucleophilic substitution of o-benzyl-2,4-dichloro-5-nitrophenol:

This step is carried out by reaction of the above mentioned dichloro compound with three molar equivalents of the sodium salt of ethylene glycol or methanol. The sodium salt can be prepared in situ with removal of the product water or can be prepared separately and used as the solid. The substitution is carried out in the parent alcohol.

bis-hydroxyethoxy compound: After 60 hours in ethylene glycol at 100°, TLC shows approximately 40% bis substitution, 30% mono substitution, and the remainder unreacted starting material. The product was isolated by stirring the reaction mixture into ice. The brown solids were collected and washed with CHCl₃/Et₂O (50:50) to remove the unreacted starting material and mono-substituted product. Yield of the golden brown crystals was 29.8%. Recrystallization from toluene yielded a pale yellow product (89% isolated), m.p. 90°–93° C.

bis-methoxy compound: The reaction was carried out in refluxing methanol. After 24 hours, reaction progress virtually halted. TLC showed no starting material, 20–30% of the mono-substituted compound, and the remainder the desired compound. The reaction was worked up by stirring into ice and filtering the precipitated product. The mono-substituted product was removed by washing with 25° toluene. Yield was 40.3%, m.p. > 260° C.

Catalytic debenzylation—hydrogenation:

bis-hydroxyethoxy compound: 6.5 g (18.6 mmoles) of O-benzyl-2-2,4-bis(2-hydroxyethoxy)-5-nitrophenol in 150 ml absolute ethanol with 13.0 ml conc. HCl (aq) and 375 mg 5% Pd/C was hydrogenated at 25 psi. Reaction was complete within 3 hours. The colorless product mixture contained a white precipitate, which was solubilized by the addition of 20 ml distilled water. The catalyst was filtered off and the filtrate reduced to dryness on the roto-vap. The product appears to be air sensitive in solution and darkened slightly during the work-up. The solid product appears stable. Yield was quantitative.

bis-methoxy compound: 0.60 g (2.08 mmoles) of O-benzyl-2,4-bis(methoxy-5-nitrophenol in 25 ml absolute ethanol with 3.0 ml conc. HCl (aq) and 45 mg 5% Pd/C was hydrogenated at 40 psi. Reaction was complete within 2 hours. Ten (10.0) ml of de-aerated distilled water was added to the product mixture and the catalyst filtered off. The filtrate was reduced to dryness on the roto-vap. This analogue also appears air sensitive in solution. Yield was quantitative.

The following examples, given in tabular form illustrate the use of the meta components of this invention in the dyeing of human hair.

TABLE III

| INGREDIENT | % by Wt. | | | | | |
|---|---|---|---|---|---|---|
| | EX. 3 | EX. 4 | EX. 5 | EX. 6 | EX. 7 | EX. 8 |
| Ethanol (Anhy.) | 35.0 | 35.0 | 35.0 | 35.0 | 35.0 | 35.0 |
| 4,6 bis(methoxy)-m-aminophenol | 1.0 | 1.0 | 1.0 | — | — | — |
| 4,6-bis(β-hydroxyethoxy) m-aminophenol | — | — | — | 1.0 | 1.0 | 1.0 |
| p-phenylenediamine | 0.88 | — | — | — | 0.68 | — |
| N,N—bis(2-hydroxyethyl) p-phenylenediamine | — | 1.43 | — | 1.11 | — | — |
| p-aminophenol | — | — | 0.95 | — | — | 0.73 |
| QS to 100 with H₂O Adjust Ph 9–9.5 with NH₄OH | | | | | | |

Each of the solutions of Examples 3 through 8 were mixed with an equal volume of 6% aqueous hydrogen peroxide to give 4 grams of dye composition. Each of these compositions was used to dye 2 gram swatches of human hair. The compositions were applied to the hair for a period of about 20 minutes at ambient temperatures.

What is claimed is:

1. As a compound a meta aminophenol useful as a meta component in an oxidation dye composition having the formula

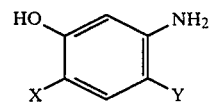

wherein X and Y are selected from the group consisting of halogen and the group OR of which R is alkyl, aminoalkyl or hydroxyalkyl, at least one of X or Y being the group OR.

2. A compound according to claim 1 wherein R is a lower alkyl, lower aminoalkyl or lower hydroxyalkyl group having from 1 to 4 carbon atoms and the halogen is chlorine.

3. A compound according to claim 2 wherein R is methyl, aminoethyl or hydroxyethyl.

4. A compound according to claim 1 having the formula

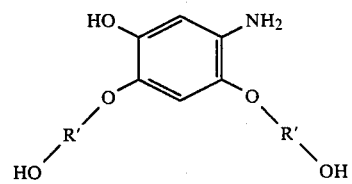

wherein R' is a divalent alkylene radical having from 1 to 4 carbon atoms.

5. A compound according to claim 1 having the formula

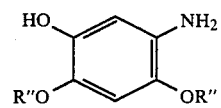

wherein R'' is a alkyl group 1 to 4 carbon atoms.

6. A compound according to claim 1 having the formula

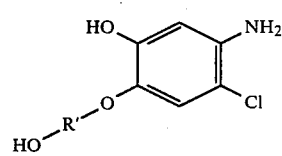

wherein R' is a divalent alkylene radical having from 1 to 4 carbon atoms.

7. An oxidation dye composition containing a para component selected from the group consisting of p-toluene diamine, p-aminophenol, p-aminodiphenylamine, 4,4'-diaminodiphenylamine, 2,6-dimethyl-p-pheylenediamine, 2,5-diaminopyridine, as well as from the class of compounds of the formula

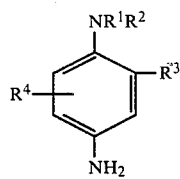 (IX)
or its non-toxic salts, in which:
R₁ is hydrogen, alkyl or hydroxyalkyl;
R₂ is hydrogen or hydroalkyl;
R₃ is hydrogen, alkyl, alkoxy or halogen; and
R₄ occupies any one of the remaining positions on the benzene radical and is hydrogen, alkyl, alkoxy or halogen and as a meta component a compound of claims 1,2,3,4,5 or 6.
* * * * *